United States Patent [19]

Nokihara et al.

[11] Patent Number: 5,431,882
[45] Date of Patent: Jul. 11, 1995

[54] APPARATUS FOR COLLECTING PEPTIDE FRAGMENT

[75] Inventors: Kiyoshi Nokihara; Rintaro Yamamoto, both of Kyoto; Yoshiyuki Togawa, Osaka; Mitsuhiro Hashimoto, Kyoto; Naoki Morita, Shiga, all of Japan

[73] Assignee: Shimadzu Corporation, Kyoto, Japan

[21] Appl. No.: 154,515

[22] Filed: Nov. 19, 1993

[30] Foreign Application Priority Data

Dec. 4, 1992 [JP] Japan .................. 4-325143

[51] Int. Cl.⁶ .............................. G01N 33/68
[52] U.S. Cl. ...................... 422/62; 422/68.1; 422/99; 422/116; 422/119; 436/86
[58] Field of Search ......... 436/86, 89; 422/62, 422/63, 67, 99, 105, 116, 119, 68.1; 530/402, 408, 410, 412

[56] References Cited

U.S. PATENT DOCUMENTS

| | | | |
|---|---|---|---|
| 4,065,412 | 12/1977 | Dreyer | 260/8 |
| 4,367,043 | 1/1983 | Sweet et al. | 356/388 |
| 5,104,973 | 4/1992 | Kondo et al. | 530/344 |
| 5,254,476 | 10/1993 | Coull et al. | 436/89 |

FOREIGN PATENT DOCUMENTS 1235600 9/1989 Japan .

Primary Examiner—David A. Redding
Attorney, Agent, or Firm—Birch, Stewart, Kolasch & Birch

[57] ABSTRACT

The present invention relates to an apparatus for collecting a peptide fragment, wherein a C-terminal peptide fragment is collected from a peptide fragment mixture resulting from specific cleavage of the peptide bond between a lysine residue and the C-terminal amino acid residue adjacent thereto. The apparatus has an immobilizing means, a cleaving means, a recovering means and a control means. According to the present invention, since the control means sequentially executes the immobilizing means, cleaving means and recovering means, no skillful work is required in peptide fragment collection, making it possible to collect the carboxyl-terminal peptide fragment with simple operation and high reproducibility.

4 Claims, 17 Drawing Sheets

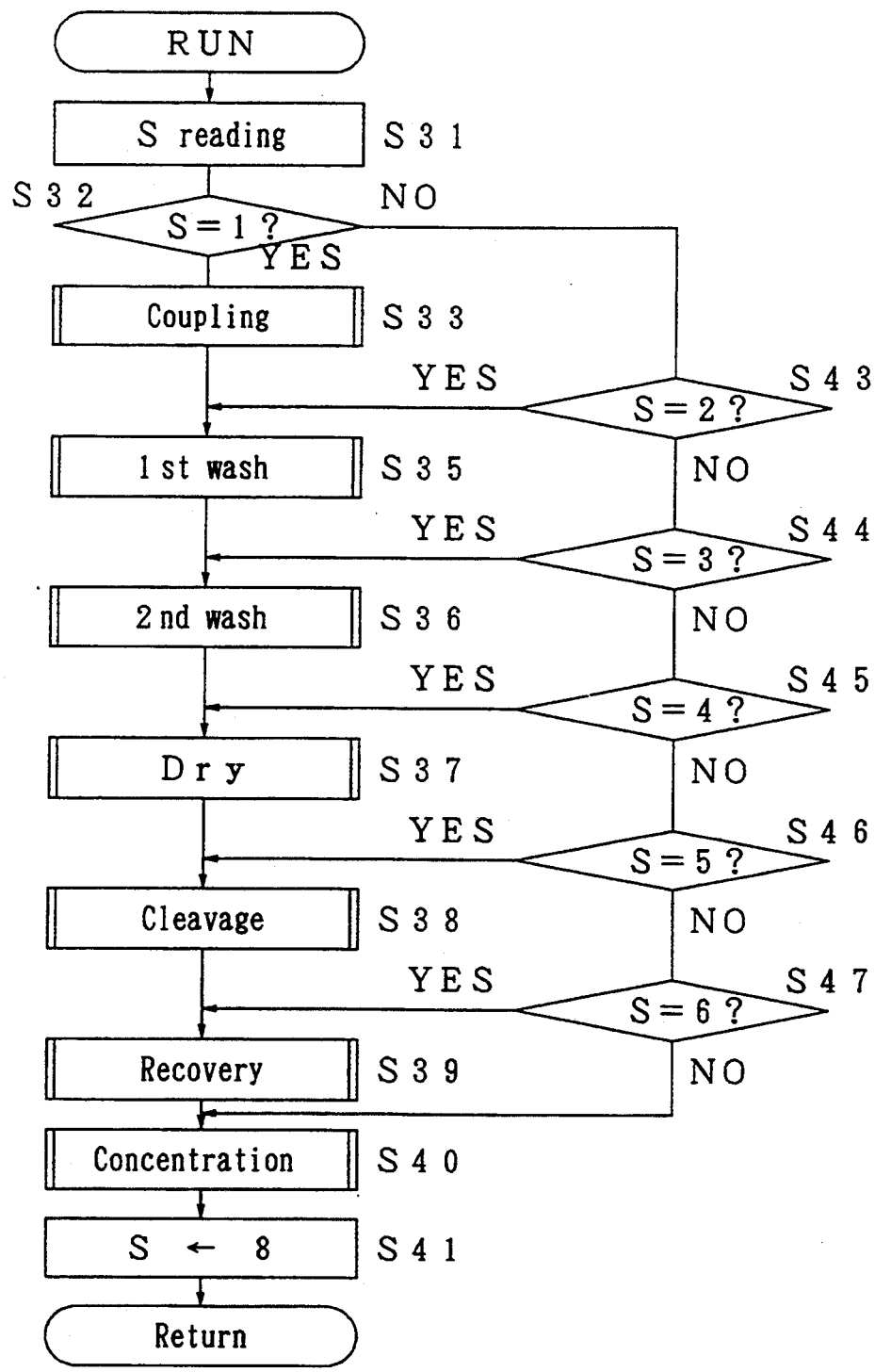
F I G. 7

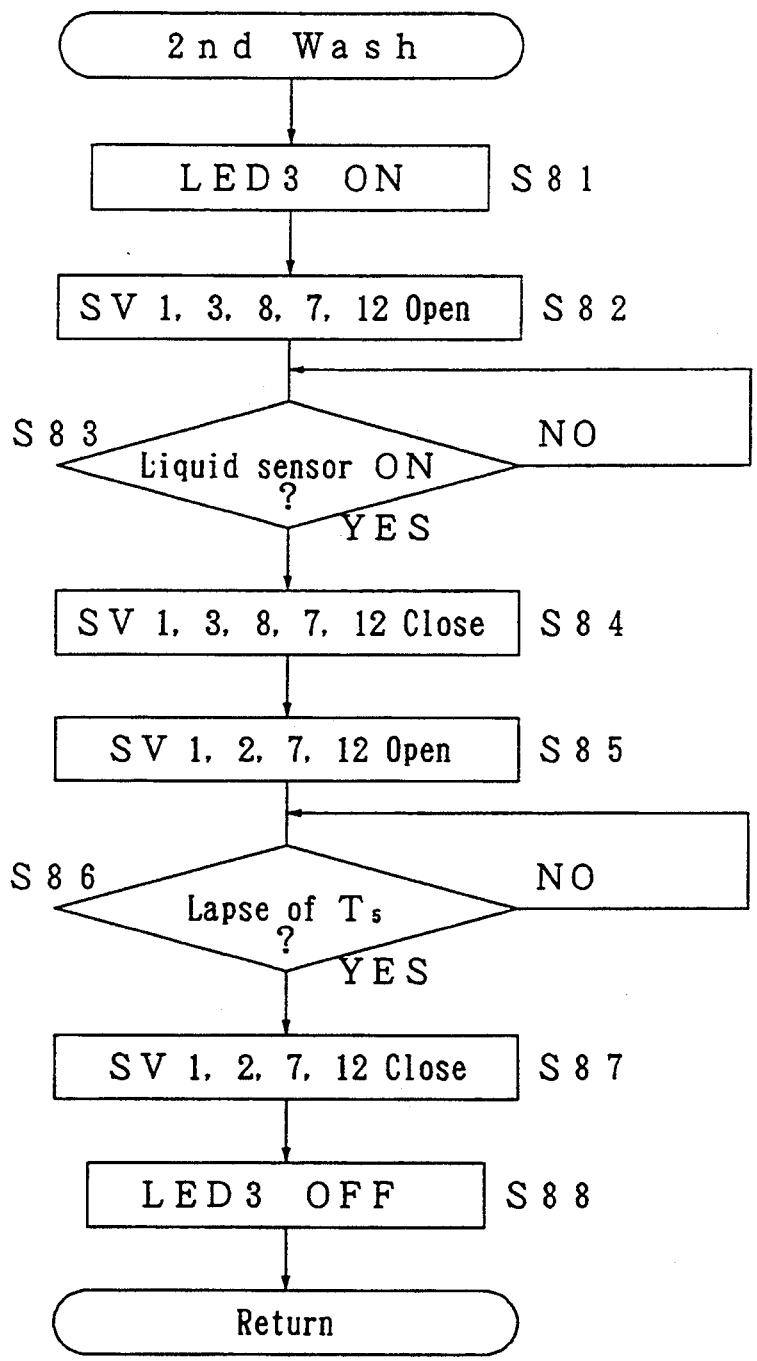
F I G. 11

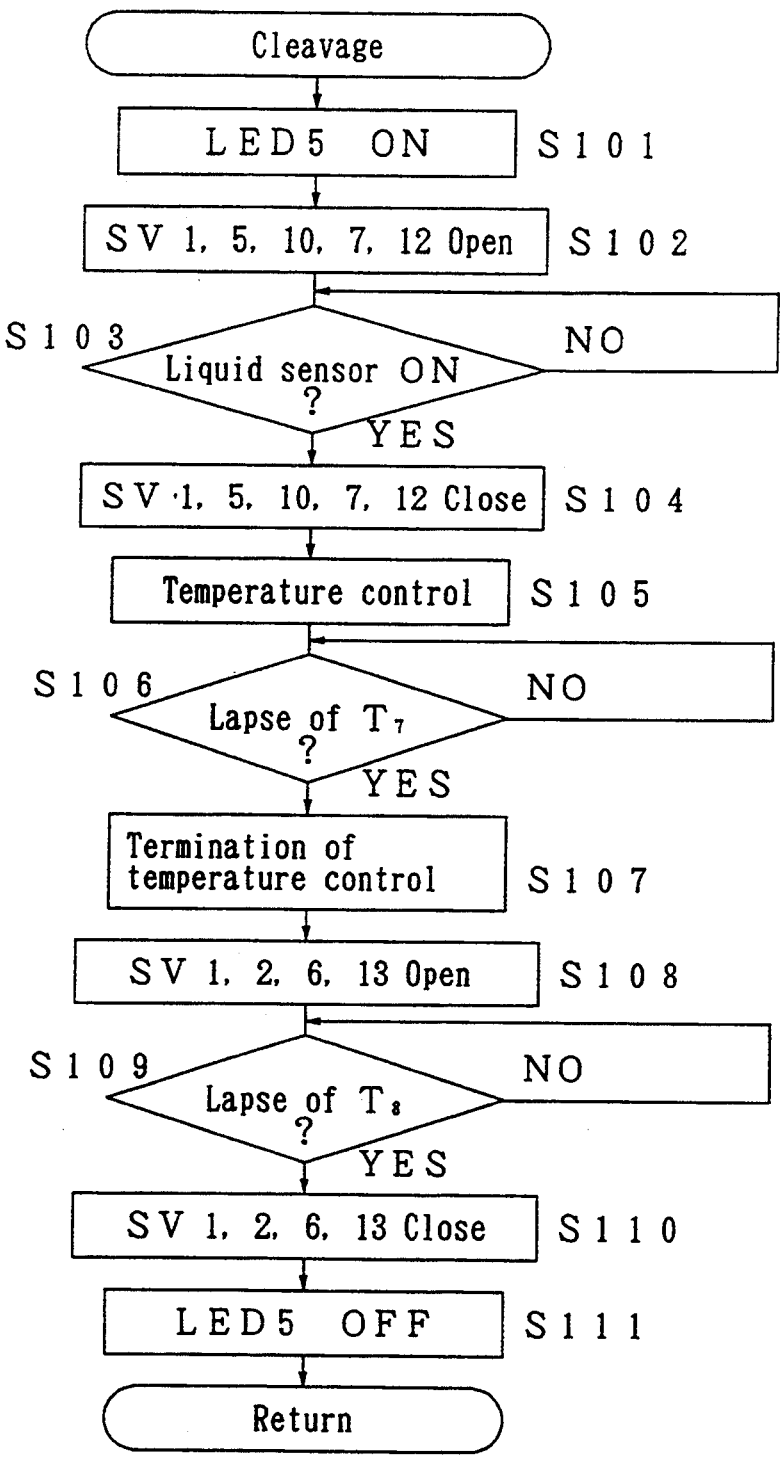
F I G. 13

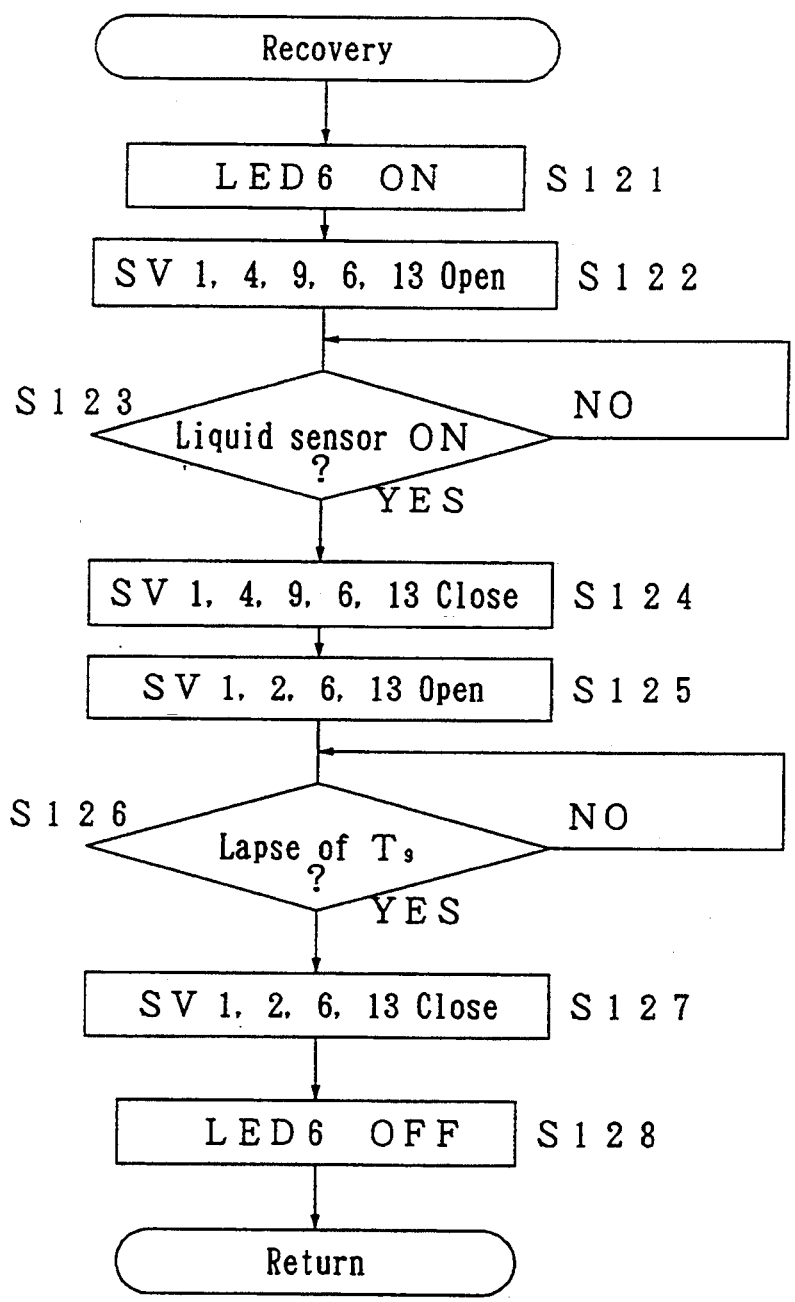
F I G. 14

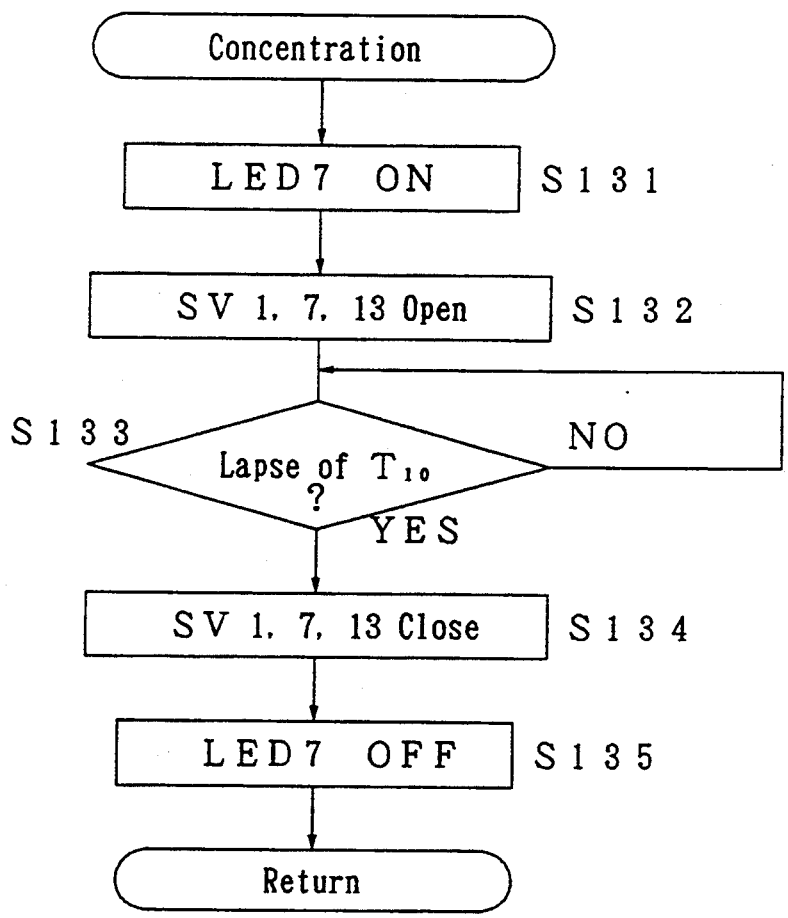
F I G. 15

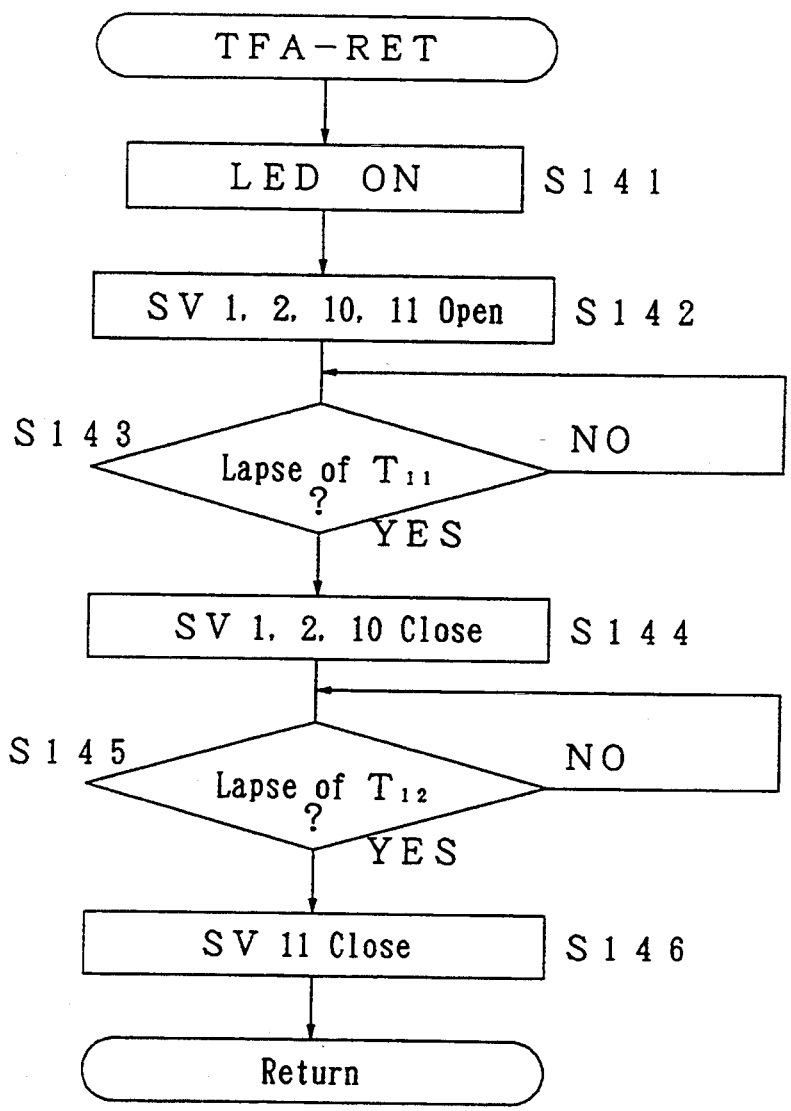
F I G. 16

APPARATUS FOR COLLECTING PEPTIDE FRAGMENT

BACKGROUND OF THE INVENTION

Field of the Invention

The present invention relates to an apparatus for collecting a peptide fragment, more specifically an apparatus for collecting the carboxyl terminal peptide fragment from a mixture of peptide fragments resulting from specific cleavage of the peptide bond between a lysine residue and the carboxyl terminal amino acid residue adjacent thereto in a polypeptide.

Discussion of the Related Art

Methods for analysis of the carboxyl terminal of a peptide (hereinafter referred to as "C-terminal") include the hydrazinolysis method, the tritium labeling method and the carboxypeptidase method. Both the hydrazinolysis method and the tritium labeling method are for determination of the end C-terminal amino acid residue only, none of which can determine all C-terminal amino acid residues. The carboxypeptidase method is based on the sequential peptide bond cleavage from the C-terminal of a polypeptide by various carboxypeptidases. Generally, this method has drawbacks such as troublesome operation, large sample volume requirements uncertainty in the amino acid sequencing and poor applicability to polypeptides having relatively long chains.

A method for peptide fragment collection for solving this problem is disclosed in Japanese Patent Laid-Open No. 1-235600. In this method, peptide bonds between lysine residues and C-terminal amino acid residues adjacent thereto are selectively cleaved. The resulting peptide fragment mixture is reacted with a solid support having on its surface a functional group capable of forming a covalent bond upon reaction with a free amino group. Subsequently, the peptide bond between the terminal residue having the amino group and the residue adjacent thereto is cleaved with an acid such as trifluoroacetic acid (TFA) and a 50%. acetonitrile-2-propanol mixture containing 0.1% TFA is added, followed by centrifugation.

The C-terminal peptide thus separated is collected and then dried in a vacuum. In this method, the C-terminal peptide is bound to the solid support at its α-amino group alone, while the other peptides are bound to the solid support at the ε-amino group of the lysine residue as well as at the N-terminal amino group. When this peptide-solid support complex is treated with an appropriate acid under appropriate conditions, the peptide bond between the amino-terminal residue and the adjacent residue alone is cleaved, and the C-terminal peptide is separated in the reaction solution with its amino-terminal residue left on the solid support, while the other peptides remaining bound to the solid support (FIG. 17).

Although the above-described method permits relatively easy separation and collection of the C-terminal peptide, it still requires skillful manual operation in several processes, including centrifugation and vacuum-drying, to collect the C-terminal peptide fragment from the peptide fragment mixture obtained by the enzyme treatment. This makes it difficult to collect the C-terminal peptide with simple operation and high accuracy, and reproducibility is low.

SUMMARY OF THE INVENTION

The object of the present invention is to provide an apparatus for collecting the C-terminal peptide fragment with simple operation and high reproducibility.

The apparatus for collecting a peptide fragment of the present invention is to collect a C-terminal peptide fragment from a peptide fragment mixture resulting from specific cleavage of the peptide bond between a lysine residue and the C-terminal amino acid residue adjacent thereto. This apparatus comprises an immobilizing means, a cleaving means, a recovering means, and a control means.

The immobilizing means is to immobilize a peptide fragment mixture to a solid support by coupling the peptide fragment mixture therewith. The cleaving means is to cleave the peptide bond after the immobilization by acid treatment. The recovering means is to recover the C-terminal peptide fragment obtained after the cleaving treatment. The control means is to sequentially execute the above means.

Specifically, in the apparatus for collecting a peptide fragment of the present invention, the control means executes the immobilizing means, cleaving means and recovering means sequentially in this order, whereby the mixture of peptide fragments is coupled with a solid support by the immobilizing means; the peptide fragment mixture coupled with the solid support is cleaved by the cleaving means using an acid treatment; and the C-terminal peptide fragments obtained after the cleavage are recovered by the recovering means.

Here, since the control means executes the immobilizing means, cleaving means and recovering means sequentially in this order, no skillful work is required in peptide fragment collection, making it possible to collect the C-terminal peptide fragment with simple operation and high reproducibility.

BRIEF DESCRIPTION OF THE DRAWING

The present invention will become more fully understood from the detailed description given hereinbelow and the accompanying drawings which are given by way of illustration only, and thus, are not limitative of the present invention, and wherein:

FIG. 7 is the flow chart of one control routine of the control system in FIG. 4;

FIG. 11 is the flow chart of one control routine of the control system in FIG. 4;

FIG. 13 is the flow chart of one control routine of the control system in FIG. 4;

FIG. 14 is the flow chart of one control routine of the control system in FIG. 4;

FIG. 15 is the flow chart of one control routine of the control system in FIG. 4;

FIG. 16 is the flow chart of one control routine of the control system in FIG. 4.

Figure 1:
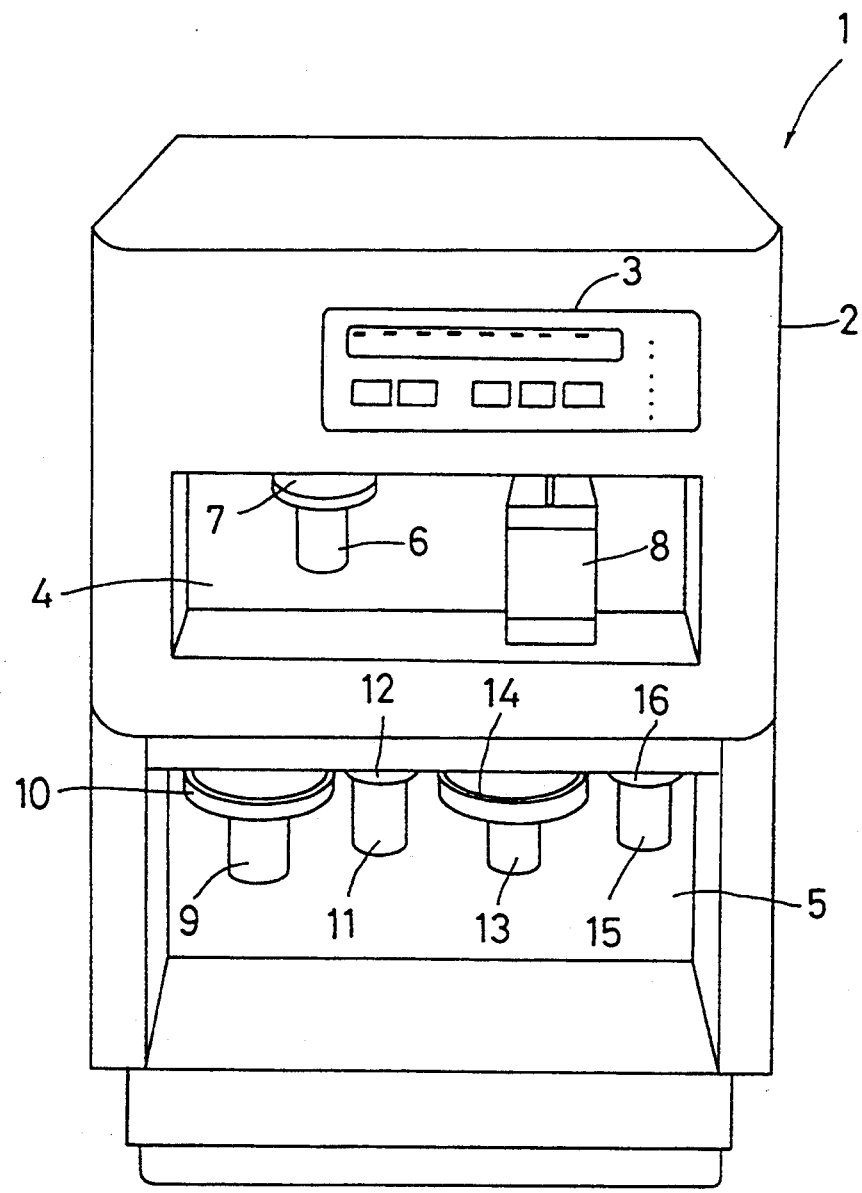
FIG. 1 is the perspective view of an example of the apparatus for collecting peptide fragments of the present invention.

The reference numerals in FIGS. 1 through 6 denote the following elements:

Element 1 is a peptide fragment collector, element 2 is a main case, element 3 is an operation panel, element 4 is a first bottle station, element 5 is a second bottle station, element 6 is a recovery bottle, element 7 is a recovery bottle holder, element 8 is a heat block, element 9 is a waste liquid bottle, element 10 is a waste liquid bottle holder, element 11 is a recovering liquid bottle, element 12 is a recovering liquid bottle holder, element 13 is a cleaving liquid bottle, element 14 is a cleaving liquid bottle holder, element 15 is a washing liquid bottle, element 16 is a washing liquid bottle holder, element 19 is a process indicator, element 20 is a key input portion, element 21 is a status indicator, element 31 is a measuring tube, element 32 is a column, element 33 is a liquid sensor, element 34 is a distribution block, element 40 is a control unit, element 41 is a temperature control unit, and element 42 is a timer.

DETAILED DESCRIPTION OF THE PREFERRED EMBODIMENT

An apparatus of the present invention is to collect a C-terminal peptide fragment from a peptide fragment mixture resulting from specific cleavage of the peptide bond between a lysine residue and the C-terminal amino acid residue adjacent thereto. This apparatus comprises an immobilizing means, a cleaving means, a recovering means, and a control means.

The peptide fragment mixture is prepared by cleaving a peptide (protein) with Lys-C specific cleavage enzyme such as API (*Achromobacter lyticus* protease I) and Endoproteinase Lys-C (trade name, manufactured by Boehringer Mannheim).

By the immobilizing means (ie, coupling means) of the present invention, the resulting peptide fragment mixture is made to couple with a solid support having a functional group capable of reacting with the α-amino group of each fragment and ε-amino group of Lys to form a covalent bond. The functional group is exemplified by the imide group, the aldehyde group, the cyano group, the acetyl group, the succinyl group, the maleyl group and the isothiocyanate group, with a preference given to the isothiocyanate group from the view point of specific reactivity with the amino group and specific post-binding cleavage. The solid support having such a functional group is a solid carrier made of a material such as porous glass, silica gel or polystyrene, and is exemplified by DITC-polyvinylalcohol.

By the cleaving means, the peptide bond between the α-amino acid residue and the amino acid residue adjacent thereto of each fragment after coupling is cleaved by acid treatment. The acid used for the acid treatment in the present invention is not limited, but preference is given to trifluoroacetic acid (TFA) because of its high volatility, high reactivity and low prevalence of side reactions.

By the recovery means, the resulting liberated C-terminal peptide fragment is recovered into the recovery bottle. The recovery means is to recover the resulting liberated C-terminal peptide fragment into the recovery bottle by flowing a recovery liquids such as 50% acetonitrile/2-propanol mixture containing 0.1% TFAs through the column.

The control means is to sequentially execute the routines for the above means.

In one embodiment of the present invention, the peptide fragment collector 1 is illustrated in FIG. 1. It comprises a box-like main case 2 and an operation panel 3 arranged in the upper front portion of the main case 2. On the front face of the main case 2 is vertically arranged a first bottle station 4 and a second bottle station 5.

The first bottle station 4 is equipped with a recovery bottle holder 7 for attaching a recovery bottle 6 for containing the recovered C-terminal peptide, and a heat block 8 for housing a column 32 described later. The second bottle station 5 is equipped with a waste liquid bottle holder 10 for attaching a waste liquid bottle 9, a recovering liquid bottle holder 12 for attaching a recovering liquid bottle 11 for containing the recovering liquid, a cleaving liquid bottle holder 14 for attaching a cleaving liquid bottle 13 for containing trifluoroacetic acid (TFA) as a cleaving reagent, and a washing liquid bottle holder 16 for attaching a washing liquid bottle 15 for containing a washing liquid.

Figure 2:
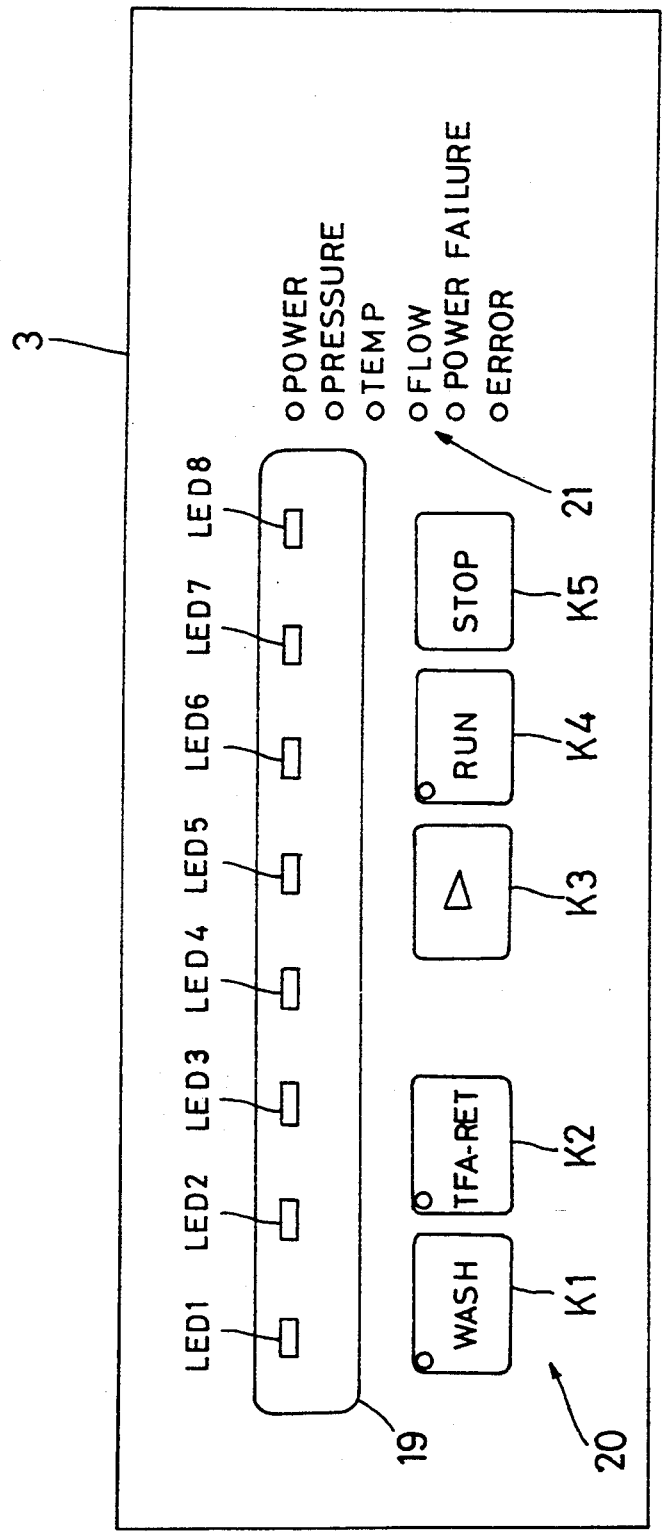
FIG. 2 is the front view of the operation panel of the example shown in FIG. 1.

As illustrated in FIG. 2, the operation panel 3 is configured with a process indicator 19 consisting of 8 units of LED 1 through LED 8 in parallel arrangement, a key input portion 20 consisting of 5 keys K1 through K5 in parallel arrangement, and a status indicator 21 consisting of six LEDs in vertical arrangement. LEDs 1 through 8 turn on in the immobilizing process, first washing process, second washing process, drying process, cleavage process, recovery process, concentration process and at completion of all processes, respectively.

Key K1 is a washing key (WASH) operated exclusively for washing the inside of tubes. Key K2 is a TFA recovery key (TFA-RET) operated for TFA recovery described later. Key K3 is a cursor key for selecting the starting process. Key K4 is a run key (RUN) for automatic progress. Key K5 is a stop key (STOP) for forced termination of a process.

Figure 3:
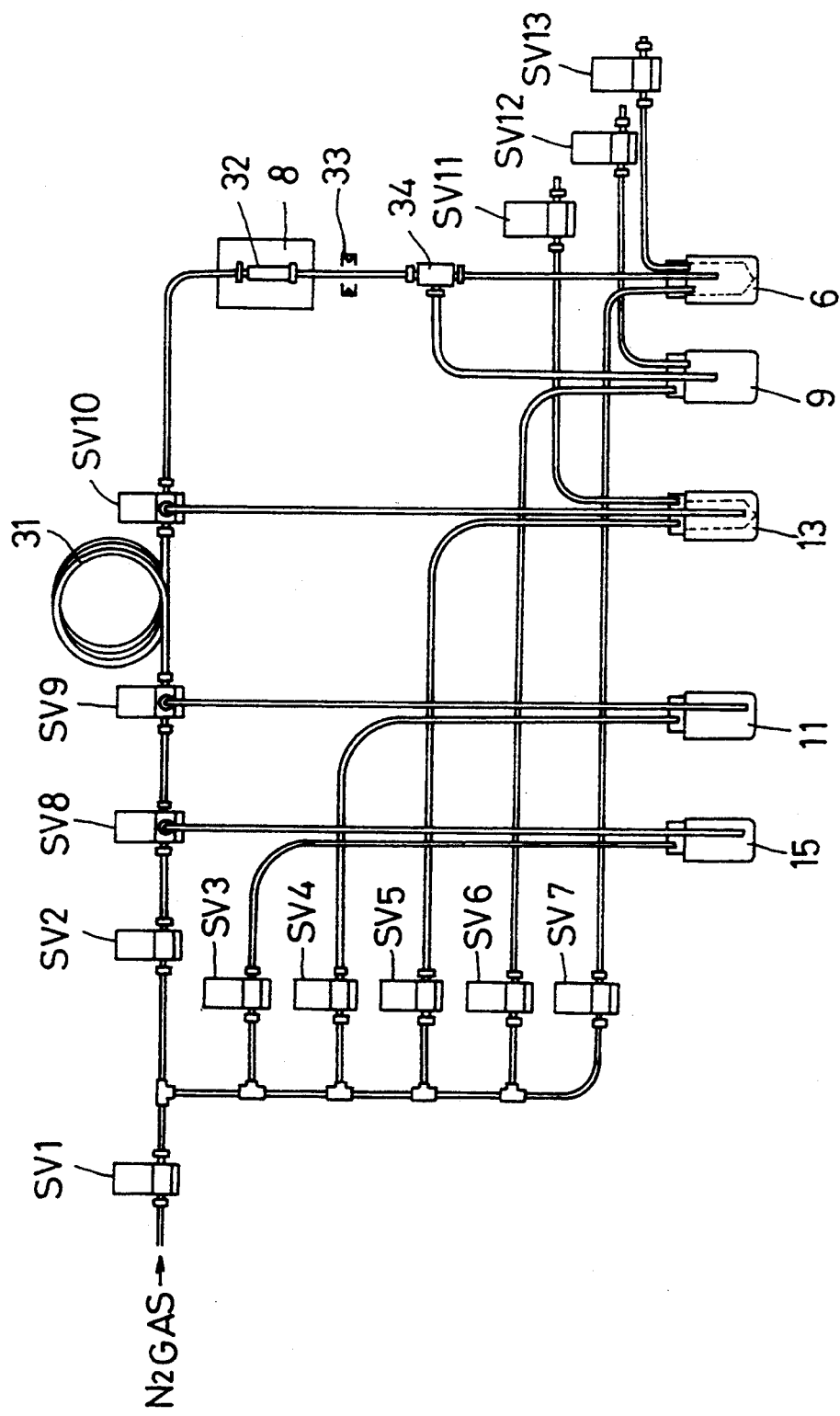
FIG. 3 is the outline of the tubing of the example shown in FIG. 1.

The main case 2 houses a tube system comprising 13 solenoid valves SV1 through SV13 as illustrated in FIG. 3. Solenoid valves SV1 through SV7 and SV11 through SV13 are normally closed two-way valves. These solenoid valves open upon power supply. Solenoid valves SV8 through SV10 are three-way valves, two of which have a normally opened inlet port and the remaining one has a normally closed outlet port. With these features, solenoid valves SV8 through SV10 have their all ports opened upon power supply and their outlet port alone closed upon power shutdown.

The inlet port of solenoid valve SV1 is connected with a nitrogen gas cylinder (not illustrated). The outlet port of solenoid valve SV1 is integrally connected with the inlet ports of solenoid valves SV2 through SV7. The outlet port of the solenoid valve SV2 is connected to the column 32 in the heat block 8 via the solenoid valve SV8, the solenoid valve SV9, a measuring tube 31 and the solenoid valve SV10.

The outlet port of the solenoid valve SV3 is connected with one end of a tube having the other end inserted in the washing liquid bottle 15. The outlet port of the solenoid valve SV4 is connected with one end of a tube having the other end inserted in the recovering liquid bottle 11. The outlet port of the solenoid valve SV5 is connected with one end of a tube having the other end inserted in the cleaving liquid bottle 13. The solenoid valve SV6 is connected with one end of a tube having the other end inserted in the waste liquid bottle 9. The outlet port of the solenoid valve SV7 is connected with one end of a tube having the other end inserted in the recovery bottle 6.

The outlet port of the solenoid valve SV8 is connected with one end of a tube having the other end inserted close to the bottom of the washing liquid bottle 15. The outlet port of solenoid valve SV9 is connected with one end of a tube having the other end inserted close to the bottom of the recovering liquid bottle 11. The outlet port of the solenoid valve SV10 is connected with one end of a tube having the other end inserted close to the bottom of the cleaving liquid bottle 13. These tubes are made of transparent resin to ensure corrosion resistance, etc.

The heat block 8 can house the column 32 for packing an enzyme-treated peptide and a solid support. The column 32 is connected with a distribution block 34 via a tube. Between the column 32 and the distribution block 34 is arranged a liquid sensor 33 for sensing the liquid passing through the tube to confirm the filling of the column 32 with the liquid. The distribution block 34 branches in two directions; one branch is connected with a tube inserted to the waste liquid bottle 9 and the other connected with a tube inserted to the recovery bottle 6, respectively. The cleaving liquid bottle 13, waste liquid bottle 9 and recovery bottle 6 are connected with the inlet ports of solenoid valves SV11, SV12 and SV13, respectively, via tubes. The outlet ports of these solenoid valves SV11, SV12 and SV13 are exposed to the atmosphere.

Figure 4:
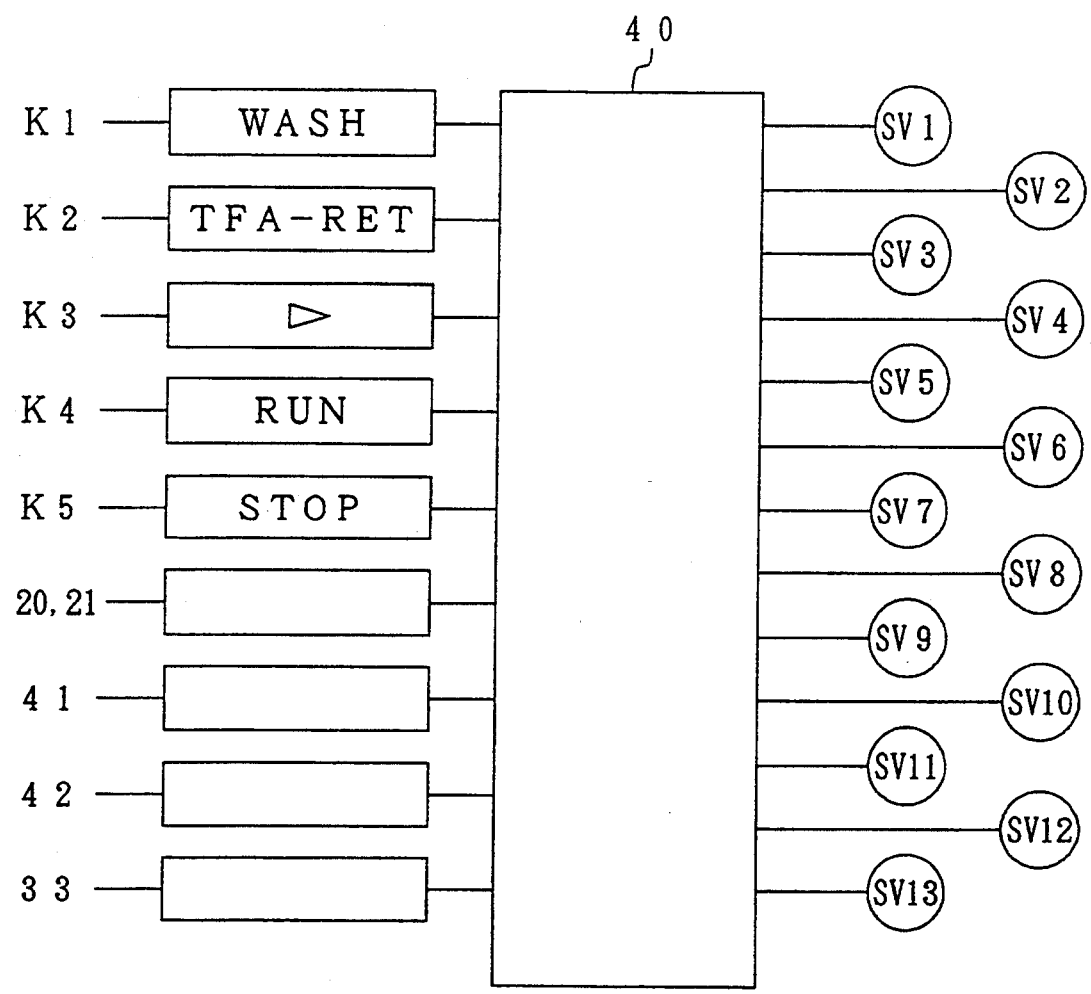
FIG. 4 is the block diagram of the control system of the example shown in FIG. 1.

The peptide fragment collector 1 has a control unit 40 as illustrated in FIG. 4. The control unit 40 comprises a micro computer having memories such as ROM and RAM. The control unit 40 is connected with solenoid valves SV1 through SV13. It is also connected with keys K1 through K5, process indicator 19 and status indicator 21, a temperature control unit 41 for controlling the temperature of the heat block 8, a timer 42 for defining processing time for each process, and a liquid sensor 33. The temperature control unit 41 is equipped with a temperature setting portion (not illustrated).

Next, the control routines of the thus-configured peptide fragment collector 1 are described by means of the flow charts given in FIGS. 5 through 16.

Before starting a control operation, the operator places reagents in respective bottles and attaches the bottles to respective holders. The washing liquid bottle 15 is previously filled with methanol or acetonitrile. The recovering liquid bottle 11 is filled with a 50% acetonitrile/2-propanol mixture containing 0.1% TFA. The cleaving liquid bottle 13 is filled with TFA.

The column 32, packed with a functionalized solid support (porous glass having the isothiocyanate group introduced therein), is attached to the heat block 8. The column 32 has been previously injected with a peptide fragment mixture treated with an enzyme (lysyl endopeptidase) containing amino acid residues. This peptide fragment mixture contains a residual portion of the urea used for the enzyme treatment.

Figure 5:
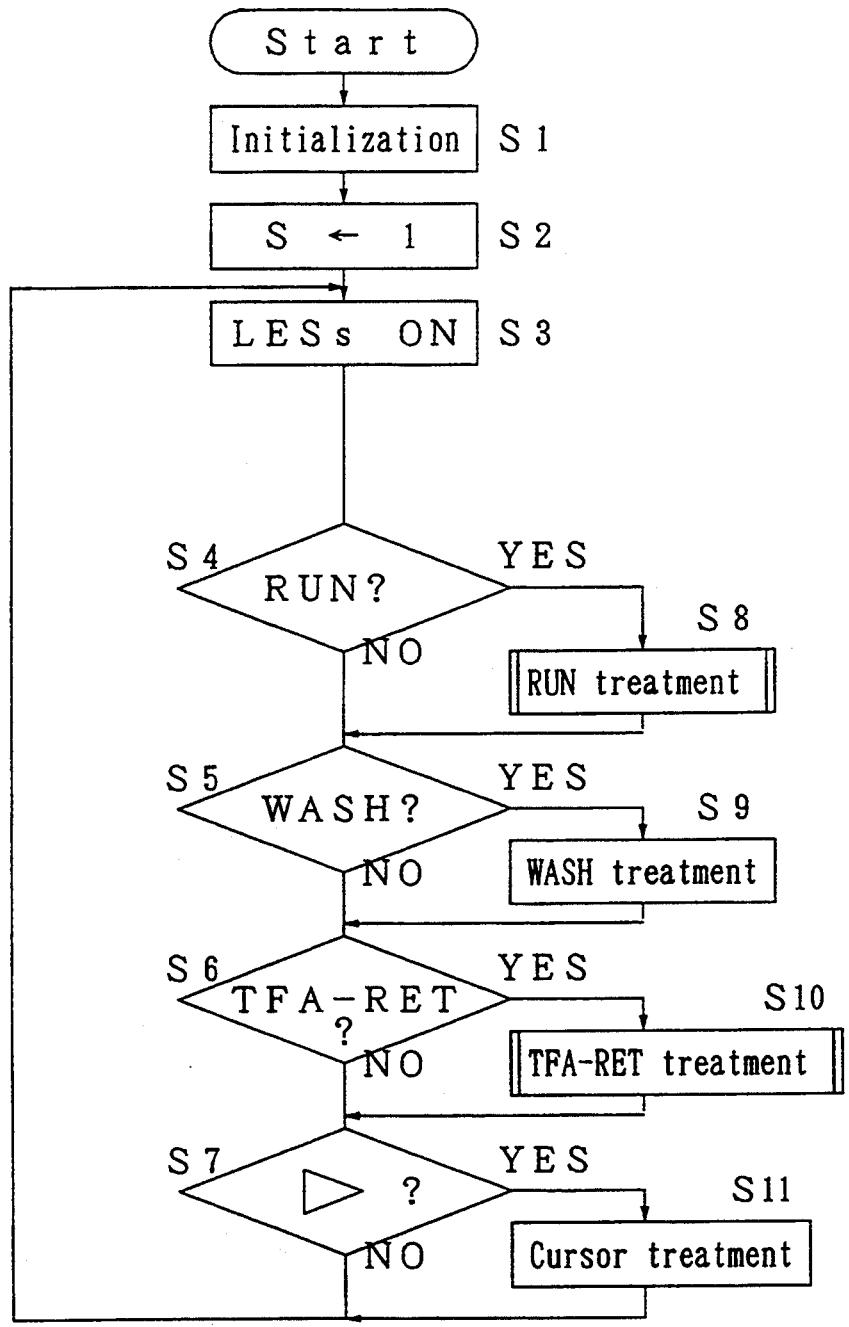
FIG. 5 is the flow chart of one control routine of the control system in FIG. 4.

At the control unit 40 of the peptide fragment collector 1, initialization is executed in step S1 by program initiation as shown in FIG. 5. Here, the memory in control unit 40, for example, is cleared. In step S2, the variable "s" showing the process status is set at "1." In step 3, an LED (initially LED 1) of the process indicator 19 turns on.

In steps S4 through S7, key judgment is repeated. Namely, in step S4, it is judged whether or not the run key K4 is in operation. In step S5, it is judged whether or not the washing key K1 is in operation. In step S6, it is judged whether or not TFA recovery key K2 is in operation. In step S7, it is judged whether or not cursor key K3 is in operation.

If the operation of the run key K4 is judged "yes" in step S4, the procedure proceeds to step S8. In step S8, the sequential processing (RUN processing) shown in FIG. 7 is executed. If the operation of the washing key K1 is judged "yes" in step S5, the procedure proceeds to step S9. In step S9, the inside of the tubes are washed. Upon sensing the operation of TFA recovery key K2 in step S6, the procedure proceeds to step S10. In step S10, the routine for TFA recovery shown in FIG. 16 is executed. If the operation of cursor key K3 is judged "yes" in step S7, the procedure proceeds to step S11. In step S11, cursor processing is executed. In this cursor processing, the variable "s" increases in response to each operation of the cursor key K3. The variable "s" returns to "1" after it is "7." The variable "s" also returns to "1" after it is "8."

In the sequential processing in step S8, the variable "s" is first read in step S31 as shown in FIG. 7. In step S32, it is judged whether or not the read variable "s" has a value of "1." When the variable "s" is judged as "1," the procedure proceeds to step S33.

In step S33, the solid support packed in the column 32 and the peptide fragment mixture are immobilized. In step S35, unbound peptides are purged and the first washing with the recovering liquid is performed, whereby the mixture of unbound peptide fragments is washed away. In step S36, the second washing with washing liquid is performed, whereby the column 32 and the inside of tube are washed. In step S37, a drying treatment with $N_2$ gas is performed. In step S38, a cleavage treatment is performed by an acid treatment with TFA. In step S39, fragments are recovered using the recovering liquid. In step S40, the recovered fragment is concentrated using $N_2$ gas.

Upon completion of these processes, the variable "s" is changed to "8" in step S41, which allows LED 8 to turn on to indicate that the sequential treatments for collection have been completed, and the procedure returns to the main routine.

When the variable "s" is judged not to be "1" in step S32 (the treatment is initiated at an intermediate process), it is judged if the variable "s" is "2" in step S43, "3" in step S44, "4" in step S45, "5" in step S46, and "6" in step S47. According to the result, the procedure proceeds from any one of steps S43 through S47 to any one of steps S35 through S39. When the variable "s" is "7," the procedure proceeds from step S47 to step S40.

Figure 8:
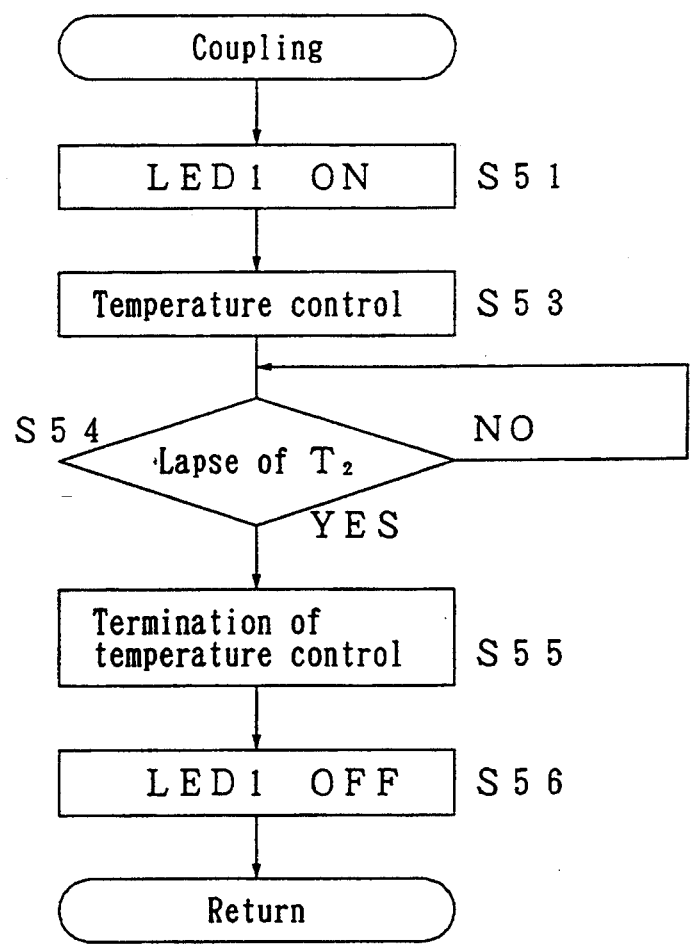
FIG. 8 is the flow chart of one control routine of the control system in FIG. 4.

In the immobilizing treatment of step S33, the LED of the RUN key turns on in step S51 of FIG. 8, whereby the operator can realize the starting of a sequential treatment. In step S53, the temperature of the heat block 8 is controlled within the temperature range from 4° C.

to 80° C. (preferably from 10° C. to 60° C.) by the temperature control unit 41. This temperature control is conducted during a preset time $T_2$ (e.g., 3 minutes to 5 hours). In other words, after the preset time $T_2$ is over in step S54, the procedure proceeds to step S55 to terminate the temperature control. In step S56, LED 1 turns off, indicating the termination of the coupling between the solid support and the peptide fragment mixture.

Figure 9:
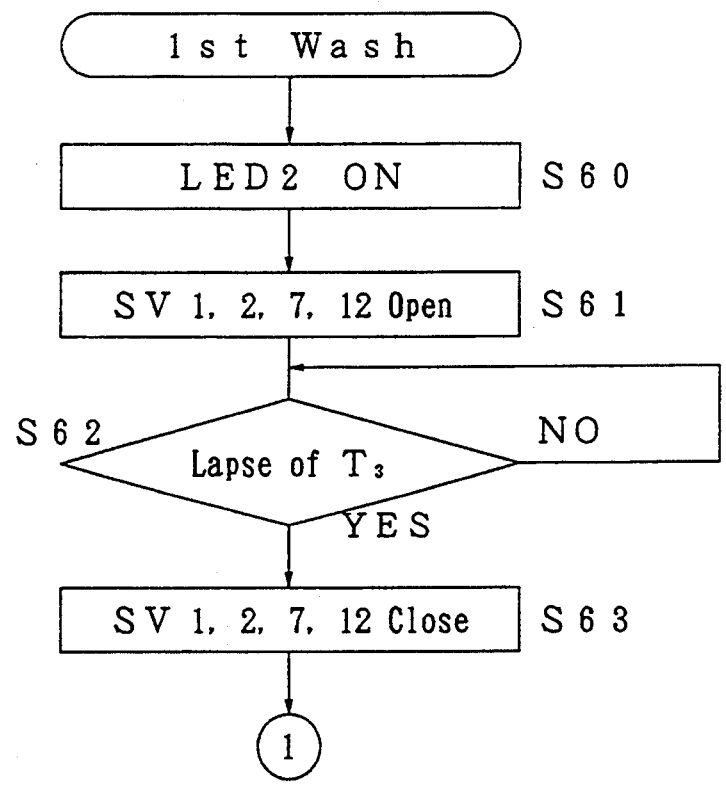
FIG. 9 is the flow chart of one control routine of the control system in FIG. 4.
Figure 10:
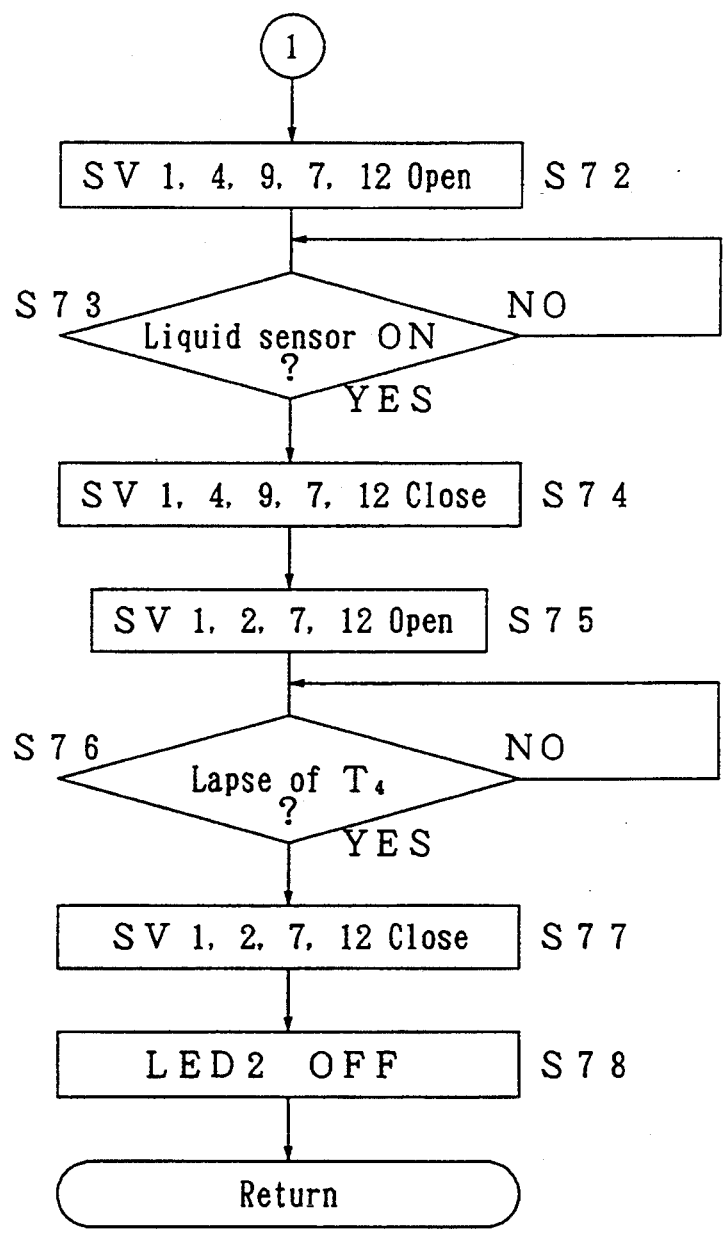
FIG. 10 is the flow chart of one control routine of the control system in FIG. 4.

In the first washing treatment of step S35 in FIG. 7, LED 2 turns on in step S60 of FIG. 9. In step S61, solenoid valves SV1, SV2, SV7 and SV12 are opened, whereby the inside of the recovery bottle 6 is pressurized with $N_2$ gas while the waste liquid bottle 9 is exposed to the atmosphere. $N_2$ gas is supplied to the column 32 via solenoid valves SV1, SV2, SV8, SV9 and SV10, whereby the uncoupled peptide in the column 32 is purged into the waste liquid bottle 9. In step S62, a preset time $T_3$ is allowed to lapse. Upon sensing the end of the preset time, the control procedure proceeds to step S63. In step S63, solenoid valves SV1, SV2, SV7 and SV12 are closed. In step S72 of FIG. 10, solenoid valves SV1, SV4, SV9, SV7 and SV12 are opened, whereby $N_2$ gas fills in the recovering liquid bottle 11 and in the recovery bottle 6. Because this results in a higher pressure in the recovering liquid bottle 11 and recovery bottle 6 than the atmospheric pressure, the recovering liquid filling the recovering liquid bottle 11 is supplied to the column 32 via the solenoid valves SV9 and SV10. In step S73, there is a delay for the liquid sensor 33 to sense the filling of the column 32 with the recovering liquid.

If the flow of recovering liquid and filling of the column 32 with recovering liquid are sensed by the liquid sensor 33, the control procedure proceeds to step S74. In step S74, solenoid valves SV1, SV4, SV9, SV7 and SV12 are closed. In step S75, solenoid valves SV1, SV2, SV7 and SV12 are opened to discharge the recovering liquid from the column 32 and tube. Because the recovery bottle 6 is pressurized and the waste liquid bottle 9 is exposed to the atmosphere, the recovering liquid filling the column 32 and tube is discharged to the waste liquid bottle 9 via the distribution block 34. In step S76, a preset time $T_4$ is allowed to lapse. When the preset time $T_4$ is over, the control procedure proceeds to step S77. In step S77, solenoid valves SV1, SV2, SV7 and SV12 are closed. After indicating the completion of the first washing process by turning off LED 2 in step S78, the control procedure proceeds to step S36 of FIG. 7.

In the second washing process of step S36 in FIG. 7, LED 3 turns on in step 81 as shown in FIG. 11. In the subsequent step S82, solenoid valves SV1, SV3, SV8, SV7 and SV12 are opened, whereby the inside of the washing liquid bottle 15 and the recovery bottle 6 are filled and pressurized with $N_2$ gas, while the inside of the waste liquid bottle 9 is exposed the atmosphere. Then the washing liquid stored in the washing liquid bottle 15 is supplied to the column 32 via solenoid valves SV8, SV9 and SV10. The washing liquid supplied to the column 32 flows toward the waste liquid bottle 9 in a way similar to the first washing process. In step S83, there is a delay for the liquid sensor 33 to sense the filling of the column 32 with washing liquid. When the liquid sensor senses the control washing liquid, the procedure proceeds to step S84. In step S84, each of the opened solenoid valves is closed. Since the operations in the steps from S85 through S88 are the same as those in steps from S75 through S78 of the first washing process, their explanation is omitted here.

Figure 12:
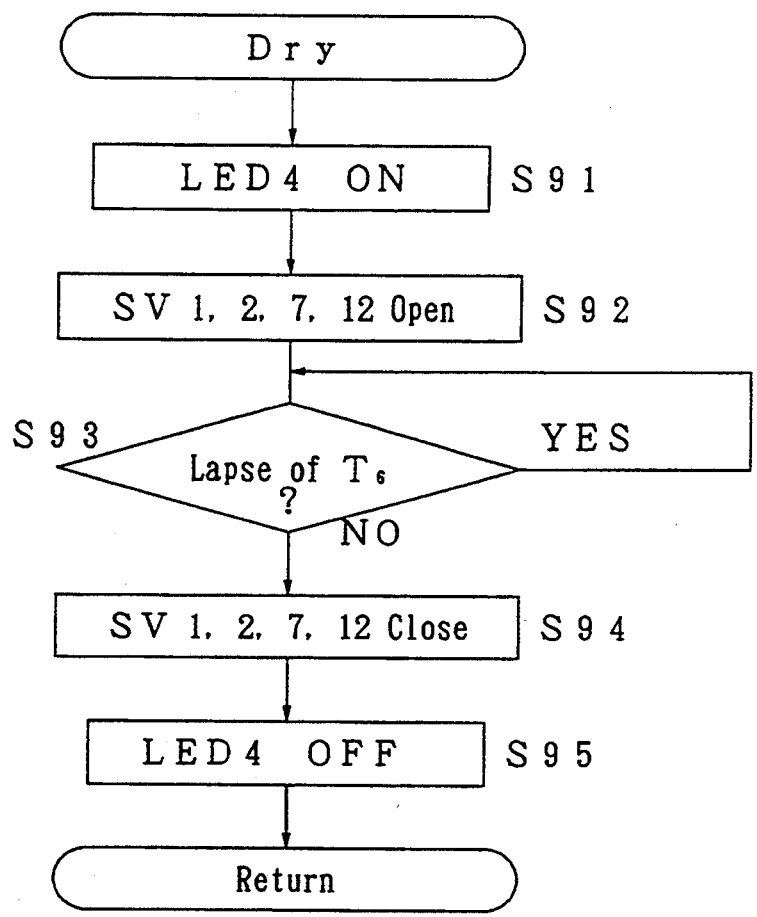
FIG. 12 is the flow chart of one control routine of the control system in FIG. 4.
Figure 17:
FIG. 17 is a schematic illustration in the chemical procedure of C-terminal fragment peptide separation in the present invention.
Figure 17:
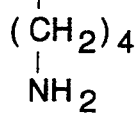
Figure 17:
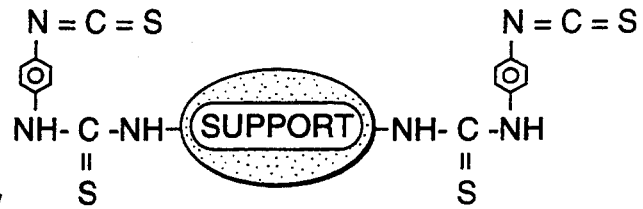
Figure 17:
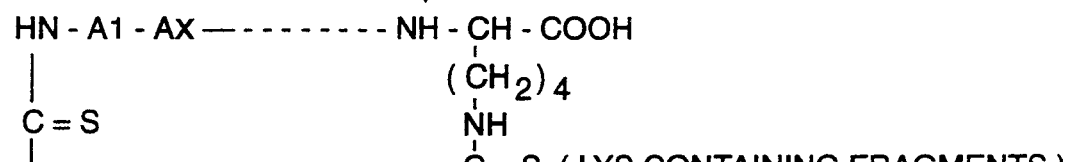
Figure 17:
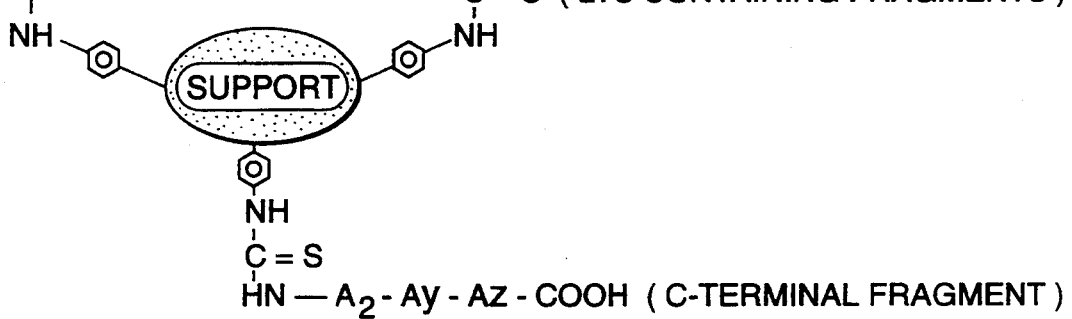
Figure 17:
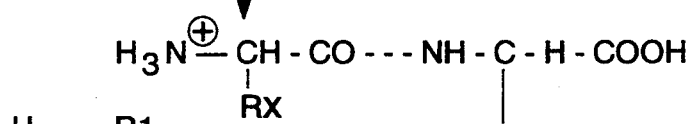
Figure 17:
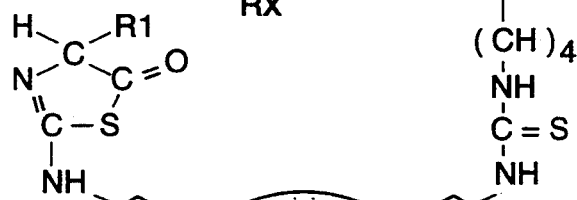
Figure 17:
Figure 17:
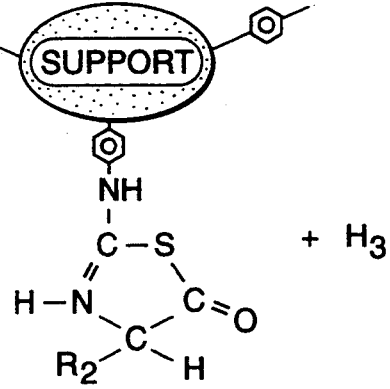
Figure 17:
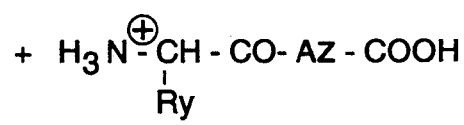
Figure 17:

In the drying process of step S37 in FIG. 7, LED 4 is turned on in step S91 of FIG. 12. In step S92, solenoid valves SV1, SV2, SV7 and SV12 are opened, and $N_2$ gas is supplied into column 32. In step S93, a preset time $T_6$ is allowed to lapse. When the preset time $T_6$ is over, the control procedure proceeds to step S94, and solenoid valves SV1, SV2, SV7 and SV12 are closed. Then the procedure proceeds to step S95 to turn LED 4 off, and to step S38 in FIG. 7. Since the drying is conducted in $N_2$ gas instead of in vacuum, the drying procedure can be simplified.

In the cleavage process of step S38 in FIG. 7, LED 5 is turned on in step S101 of FIG. 13. In step S102, solenoid valves SV1, SV5, SV10, SV7 and SV12 are opened, whereby TFA stored in the cleaving liquid bottle 13 is supplied into the column 32 via the solenoid valve SV 10. in step S103, it is waited for the liquid sensor 33 to sense the TFA liquid. When the column 32 is filled with TFA, and the liquid sensor 33 senses TFA liquid, the procedure proceeds to step S104. In step S104, the solenoid valves SV1, SV5, SV10, SV7 and SV12 are closed.

In step S105, the temperature of the heat block 8 is controlled by the temperature control unit 41. The temperature is adjusted in the range of 20° C. to 80° C., preferably 30° C. to 60° C. In step S106, a preset time $T_7$ (5 minutes to 1 hour) is allowed to lapse, and the control procedure proceeds to step S107 by the judgement that the preset time $T_7$ is over. In step S107, temperature control is terminated. In step S108, the solenoid valves SV1, SV2, SV6 and SV13 are opened, whereby the inside of the waste liquid bottle 9 is pressurized and the inside of the recovery bottle 6 is exposed to the atmosphere. Then $N_2$ gas flows through the column 32 and distribution block 34 and spouts into the recovery bottle 6, whereby the column 32 is purged. In step S109, the lapse of the preset time $T_8$ is waited. When the preset time $T_8$ is over, the control procedure proceeds to step S110 to close the solenoid valves SV1, SV2, SV6 and SV13. After LED5 is turned off in step S111, the control procedure proceeds to step S39 in FIG. 7.

In the recovery process of step S39 in FIG. 7, LED6 is turned on in step S121 of FIG. 14. In step S122, the solenoid valves SV1, SV4, SV9, SV6 and SV13 are opened, whereby the inside of the recovering liquid bottle 11 and waste liquid bottle 9 is pressurized, and the inside of the recovery bottle 6 is exposed to the atmosphere. Thus, the recovering liquid in the recovering liquid bottle 11 is supplied into the column 32 through the solenoid valve SV9, measuring tube 31 and solenoid valve SV10. In step S123, a time lapse is allowed for the liquid sensor 33 to sense the recovering liquid. When the liquid sensor 33 senses the recovering liquid, the control procedure proceeds to step S124. In step S124, solenoid valves SV1, SV4, SV9, SV6 and SV13 are closed, followed by opening of solenoid valves SV1, SV2, SV6 and SV13 in step S125. Then the recovering liquid for the C-terminal peptides cleaved in the column 32 is recovered into the recovery bottle 6 via the distribution block 34. In step S126, the lapse of the preset time $T_9$ is waited. When the preset time $T_9$ is over, the procedure proceeds to step S127, and the solenoid valves SV1, SV2, SV6 and SV13 are closed. By the completion of these procedures, the residual C-terminal peptides in the column 32 have efficiently been recovered in the recovery bottle 6. After LED6 is turned off in step S128, the procedure proceeds to step S40 in FIG. 7.

In the concentration treatment of step S40 in FIG. 7, LED 7 is turned on in step S131 of FIG. 15. In step 132, the solenoid valves SV1, SV7 and SV13 are opened, whereby $N_2$ gas flows into the recovery bottle 6 to evaporate and concentrate the recovering liquid therein. In step S133, the lapse of the preset time $T_{10}$ is waited. This preset time is, for example, about 3 hours. In step S134, the solenoid valves SV1, SV7 and SV13 are closed. After LED 7 is turned off in step S135, the control procedure proceeds to step S41 in FIG. 7.

In step S41, the variable "s" is set at "1" in order to turn on LED 8 in step S3 as shown in FIG. 5.

At the time of completion of these sequential treatments, the inside of the cleaving liquid bottle 13 remains to be pressurized, and TFA remains in the tube connecting the solenoid valve SV10 and the cleaving liquid bottle 13. In order to remove the residual TFA in the tube, the TFA recovery key K2 is operated.

In the TFA recovery treatment of step S10 in FIG. 5, the LED for the TFA recovery key K2 is turned on in step S141 of FIG. 16. In step S142, the solenoid valves SV1, SV2, SV10 and SV11 are opened, whereby the inside of the cleaving liquid bottle 13 is exposed to the atmosphere, and $N_2$ gas flows into the cleaving liquid bottle 13 via the solenoid valve SV10, which allows the recovery of the residual TFA into the cleaving liquid bottle 13. In step S143, a preset time $T_{11}$ is allowed to lapse. The preset time $T_{11}$ is long enough to recover the residual TFA in the tube. When the preset time $T_{11}$ is over, the control procedure proceeds to step S144.

In step S144, the solenoid valves SV1, SV2 and SV10 are closed. In step S145, a preset time $T_{12}$ is allowed to lapse. The preset time $T_{12}$ is long enough to restore the atmospheric pressure in the cleaving liquid bottle 13. When the preset time $T_{12}$ is over, the control procedure proceeds to step S146. After the solenoid valve SV11 is closed in step S146, the control procedure returns to the main routine.

To interrupt the above-described sequential treatment, the stop key K5 may be pressed. Upon stop key K5 operation, an interruption sets in, and works the stop procedure shown in FIG. 6.

Figure 6:
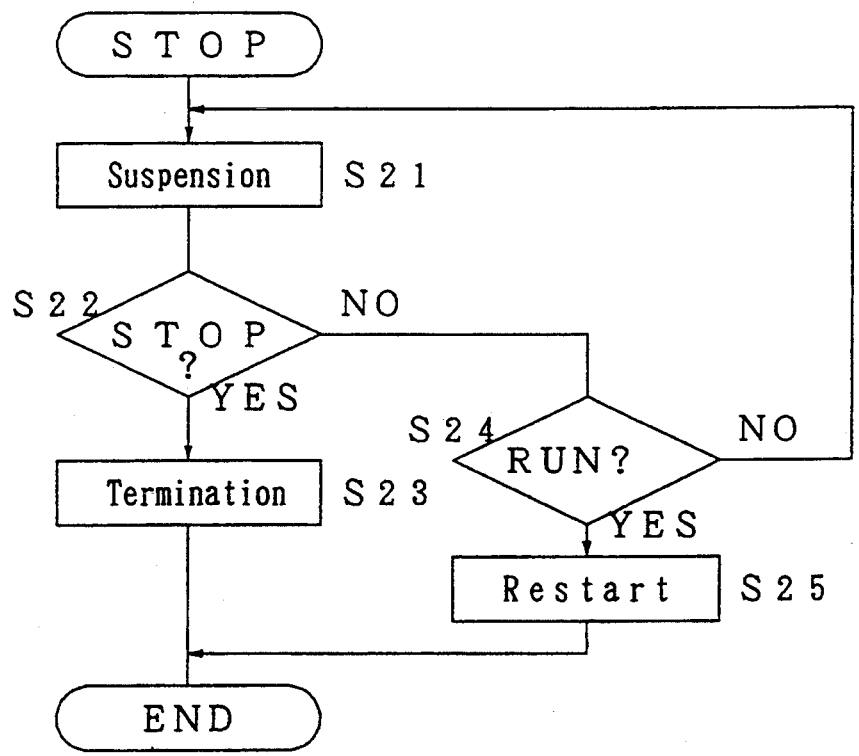
FIG. 6 is the flow chart of one control routine of the control system in FIG. 4.

In step S21 in FIG. 6, an operation in the sequential treatments is suspended. In step S22, it is judged whether or not the stop key K5 has been operated again. Upon sensing no operation of the stop key K5, the procedure proceeds to step S24. In step S24, it is judged whether or not the run key K4 has been operated. When the run key K4 has not been operated, the procedure returns to step S21, with the treatment being suspended.

Here, when the stop key K5 is operated again, the program shifts from step S22 to step S23. In step S23, the program counter is changed so that the next routine will be step S2 in FIG. 5 to return to the starting process. When the run key K4 is operated, the program shifts to step S25. In step 25, suspended action is restored.

In the above-described example, the C-terminal peptide fragment can be collected from a peptide fragment mixture by a simple operation comprising: the column 32 is packed with a solid support; a peptide fragment mixture is injected; the column is attached to the heat block 8; and each bottle is attached to the corresponding holder. This allows easy collection of the C-terminal fragment from a peptide without skill with good reproducibility.

Also, since the TFA recovery process permits the recovery of residual reagents in the tube, TFA vapor diffusion from the tube can be reduced, leading to reduction of troubles such as corrosion.

In addition, since the liquid flowing from the column 32 is divided by selectively pressurizing the waste liquid bottle 9 and the recovery bottle 6, or exposing them to the atmosphere, it is not necessary to install any solenoid valve on the flow-dividing pathway. This can reduce the downstream dead volume of the reaction column etc., thus permitting long-term use of such samples and reagents as urea which crystallizes upon drying.

In the above example, the routines are configured so that the TFA recovery procedure can be executed independently. In another preferred embodiment of the present invention, the recovery procedure is automatically performed after the completion of each cleavage treatment with TFA solution.

The present invention being thus described, it will be obvious that the same may be varied in many ways. Such Variations are not to be regarded as a departure from the spirit and scope of the invention, and all such modifications as would be obvious to one skilled in the art are intended to be included within the scope of the following claims.

What is claimed is:

1. An apparatus for collecting a peptide fragment, wherein a C-terminal peptide fragment is collected from a peptide fragment mixture resulting from specific cleavage of the peptide bond between a lysine residue and the C-terminal amino acid residue adjacent thereto, comprising an immobilizing means by which said peptide fragment mixture is coupled with a solid support; a cleaving means by which said peptide fragment mixture coupled with said solid support by said immobilizing means is cleaved with acid treatment; a recovering means by which a peptide fragment cleaved by said cleaving means is recovered; and a control means by which said immobilizing means, said cleaving means and said recovering means are executed in the order of immobilizing, cleaving, and recovering by a sequential processing.

2. The apparatus according to claim 1, wherein said sequential processing comprises immobilizing the peptide fragment mixture onto the solid support, washing the immobilized peptide fragment, drying the washed peptide fragment, cleaving the dried peptide fragment, recovering the cleaved peptide fragment, and concentrating the recovered peptide fragment.

3. The apparatus according to claim 2, wherein in each treatment of the immobilizing, the washing, the drying, the cleaving, the recovering and the concentrating, an LED turns on at the starting of each treatment and turns off at the termination.

4. The apparatus according to claim 1, wherein said recovering means comprises a distribution block, a gas pressurization means, a waste liquid bottle, and a recovery bottle, whereby said peptide fragment is collected into said recovery bottle via said distribution block by pressurizing said waste liquid bottle with a gas from said gas pressurization means.

* * * * *